United States Patent
Martin

(10) Patent No.: US 6,921,899 B2
(45) Date of Patent: Jul. 26, 2005

(54) GAS CELL WITH REFLECTED LIGHT BUNDLES

(75) Inventor: Hans Göran Evald Martin, Delsbo (SE)

(73) Assignee: Senseair AB (SE)

( * ) Notice: Subject to any disclaimer, the term of this patent is extended or adjusted under 35 U.S.C. 154(b) by 348 days.

(21) Appl. No.: 10/258,166

(22) PCT Filed: Apr. 26, 2001

(86) PCT No.: PCT/SE01/00901

§ 371 (c)(1),
(2), (4) Date: Oct. 17, 2002

(87) PCT Pub. No.: WO01/81901

PCT Pub. Date: Nov. 1, 2001

(65) Prior Publication Data

US 2003/0058439 A1 Mar. 27, 2003

(30) Foreign Application Priority Data

Apr. 26, 2000 (SE) .............................. 0001509

(51) Int. Cl.[7] .......................... G01J 5/02; G01N 15/06; G01N 21/49; G01N 21/85
(52) U.S. Cl. ...................... 250/349; 250/343; 250/353; 250/574; 250/575; 250/576
(58) Field of Search ................................ 250/343, 349, 250/353, 574–576; 356/433–437

(56) References Cited

U.S. PATENT DOCUMENTS

| | | | |
|---|---|---|---|
| 5,009,493 A | 4/1991 | Koch et al. ................. 350/619 |
| 5,060,508 A * | 10/1991 | Wong ......................... 73/31.02 |
| 5,550,375 A * | 8/1996 | Peters et al. ................ 250/343 |
| 5,726,752 A * | 3/1998 | Uno et al. ................... 356/246 |
| 5,973,326 A * | 10/1999 | Parry et al. ................. 250/343 |
| 6,016,203 A * | 1/2000 | Martin ........................ 356/432 |

FOREIGN PATENT DOCUMENTS

| | | |
|---|---|---|
| DE | 4214840 | 11/1993 |
| WO | 97/10460 | 3/1997 |
| WO | 98/09152 | 3/1998 |

OTHER PUBLICATIONS

International Search Report.

* cited by examiner

Primary Examiner—David Porta
Assistant Examiner—Frederick Rosenberger
(74) Attorney, Agent, or Firm—Ostrolenk, Faber, Gerb & Soffen, LLP

(57) ABSTRACT

The invention relates to a gas cell (2') that includes a cavity (20) for a chosen gas volume, a light source (30), and one or more light bundle receiving units or detectors (21, 22, 23, 24, 25). The cavity (20) is formed by and delimited by, inter alia, a first partially elliptical mirror surface (20a) and two partially elliptical mirror surfaces, a second (20b) and a third (20c), which are opposed to said first mirror surface (20a) and which are so orientated in relation to each other that a light bundle (130a, 130b) will be reflected by said mirror surfaces (20a, 20b, 20c) so as to form an optical measurement path extremity, and terminate in a light-receiving unit (21, 22, 23, 24, 25) allocated to a chosen measurement path extremity. The light source (30) is disposed in one end region of said cavity (20) and a reflector (30a, 30b) which functions to cause emitted light bundles to converge towards a focusing point (F) is also disposed in said one end region.

18 Claims, 2 Drawing Sheets

GAS CELL WITH REFLECTED LIGHT BUNDLES

FIELD OF INVENTION

The present invention relates generally to a gas cell and more specifically to a gas cell of the kind that includes a cavity for accommodating a chosen gas volume, a light source, and units for receiving one or more light beams or bundles of light rays.

More particularly, the invention relates to a gas cell of this kind in which the cavity is formed and defined by a first, partially elliptical mirror surface that faces towards two partially elliptical mirror surfaces, i.e. a second and a third mirror surface.

These elliptical mirror surfaces are so orientated in relation to each other that a light beam emitted from the light source will be reflected by said mirror surfaces so as to provide an optical measuring path extremity and terminate in a receiving unit intended for a selected path extremity.

By the expression "partially elliptical" shall be understood solely a part of a full elliptical shape on the one hand and an elliptical shape that conforms essentially with a mathematical elliptical shape on the other hand.

DESCRIPTION OF THE BACKGROUND ART

It has long been known to use electromagnetic waves in connection with absorption spectroscopy, and then particularly light beams or bundles of light rays (light bundles) whose frequencies lie within the infrared range, and to use different types of detector elements.

In the case of gas sensors that are based on absorption technology, the light beams shall be permitted to pass through a gas sample contained in a cell cavity, wherewith a given volume of a selected gas will result in frequency-dependent absorption of the light beams.

A gas detector is thus adapted to detect the frequency spectrum of the light beams for a relevant gas or gas concentration within the cavity, and the gas or gas concentration can be determined by evaluating the intensity of the detected light beam in relation to a chosen intensity for the incident light beams and the absorption coefficient of the light concerned or the electromagnetic wavelength in the gas concerned.

With regard to the features of the present invention, it can be mentioned that it is known to compress a gas cell with respect to its physical dimension, by allowing the light beams to be reflected a number of times within the cavity, thereby to obtain a relatively long optical measurement path extremity (wavy length) or a relatively long absorption path extremity relative to the internal dimensions of the gas cell or the cavity.

The absorption cell or gas cell disclosed in Patent Publication U.S. Pat. No. 5,009,493 is an example of a gas cell that is designed to provide an adapted long absorption path extremity or an optical measuring path extremity within a defined or delimited cavity, where incoming light beams (or light bundles) shall be reflected a number of times within the cavity before being exited therefrom and thereafter fall on a light detector.

In gas cells of this kind, it is usual to allow incoming light beams to pass into the cavity via a first opening, and to exit the beams from the cavity via a second opening, therewith enabling a detector that is used in the present context to consist of a separate unit that is preferably mounted on the gas cell in connection with the second opening.

The cavity of the gas cell is formed normally by at least a first and a second part, whose inner surfaces may be treated to provide surfaces that strongly reflect the incoming light beams or light bundles.

This surface treatment normally comprises coating the inner surface with one or more layers of metal, wherewith the reflecting surfaces are formed by the last metal layer applied.

The metal and procedure chosen for this coating process will depend on the desired optical qualities of the surfaces and also on the optical wavelength or wavelengths that shall be reflected by said surfaces. The material in the gas cell body shall also be taken into consideration.

With regard to the significant characteristic features and properties of the present invention, mention shall also be made to an example of an earlier known gas sensor in which incoming light beams or light bundles are reflected a number of times within the cavity in accordance with a predetermined pattern.

In this respect, reference is made to a gas sensor that is illustrated and described in International Patent Application PCT/SE96/01448, Publication No. WO97/10460 and the International Patent Application PCT/SE97/01366, Publication No. WO98/09152, from which the present invention can be considered to constitute a development.

SUMMARY OF THE INVENTION

Technical Problems

When taking into consideration the technical deliberations that a person skilled in this particular art must take in order to provide a solution to one or more technical problems that he/she encounters, it will be seen that it is necesssary initially to realise the measures and/or the sequence of measures that must be taken to this end on the one hand, and on the other hand to realise which means is/are required to solve one or more of said problems. On this basis, it will be evident that the technical problems listed below are highly relevant to the development of the present invention.

When considering the present state of the art as described above, it will be seen that in respect of a gas cell of the kind described in the introduction a technical problem resides in creating conditions which enable a chosen adapted optical measuring path extremity to be longer than the measuring path extremities that can be obtained with the aforesaid international patent publications below a limited increase in size of the cavity used.

Another technical problem resides in realising the significance of and the advantages gained by allowing said light source to be disposed within one end-region of said cavity, so as to be able to create conditions that provide advantages over those that can be afforded by earlier known technology.

A further technical problem resides in realising the significance of and the advantages afforded by disposing in said one end-region a reflector that causes the emitted light bundles to converge.

It will also be seen that a technical problem resides in realising the significance of and the advantages afforded by adapting said reflector so as to cause the light bundles to converge towards a focusing point which becomes located within the cavity.

Another technical problem is one of realising the significance of and the advantages gained by allowing said focusing point to be situated adjacent a flat mirror part associated with said cavity.

Another technical problem is one of realising the significance of and the advantages afforded by allowing a virtual focusing point created via said flat mirror part to be located outside said cavity.

A further technical problem is one of realising the significance of and the advantages afforded by disposing the flat mirror part adjacent a first delimiting surface of said first, partially elliptical, mirror surface.

Another technical problem is one of realising the significance of and the advantages associated with allowing said reflector to be comprised of a partially elliptical section adjacent a second delimiting surface of said first, partially elliptical, mirror surface.

It will also be seen that a technical problem resides in realising the significance of allowing the reflector to be comprised of a partially elliptical section formed by a wall portion placed in the cavity.

Another technical problem is one of realising the significance of and the advantages gained by the ability to create in a gas cell of the kind concerned conditions which will enable a thin cavity to be chosen and said cavity to be formed by at least two mutually co-acting parts.

A technical problem also resides in realising the significance of and the advantages associated with allowing a gas connection to the cavity to be disposed adjacent the aforesaid flat mirror part.

Yet another technical problem is one of realising the significance of and the advantages gained by allowing a gas connection to the cavity to be disposed adjacent a light source and adjacent the wall-part placed in the cavity.

Another technical problem resides in the ability to realise the significance of and the advantages gained by enabling the light bundle to be reflected from said virtual focusing point to a border region between the second and the third partially elliptical mirror surface and to allow a first part of the light bundle, reflected by the second mirror surface, to be allocated to a first optical measuring path extremity, and to assign another part of the light bundle, reflected by the third mirror surface, to a second optical measuring path extremity.

In the case of a gas cell of the kind described in the introduction, a technical problem resides in the ability to realise the significance of and the advantages gained by means for deflecting a direct-acting light bundle from the light source disposed adjacent said light source and directed towards the flat mirror part, such as to be able to form a further optical, although short, measuring path extremity.

Another technical problem resides in the ability to realise the significance of and the advantages associated with allowing cavity-associated active optical surfaces to be concentrated on a respective side of the light source and towards partially elliptical reflector-adapted sections and optical surfaces that converge towards a focusing point and a surface region orientated between the three partially elliptical mirror surfaces.

Another technical problem resides in the ability to realise the significance of and the advantages associated with allowing said means to be adapted for shadowing direct-active light bundles from the light source to the cavity-associated light detectors.

A further technical problem resides in the ability to create with the aid of simple means and with a gas sensor of limited form conditions such that the gas sensor can be readily caused to measure moisture content, or water vapour concentration, or, alternatively, the presence of and the concentration of some other chosen gas, such as carbon dioxide, carbon monoxide, nitrous oxide, etc.

Solution

The present invention is thus based on a gas cell of the kind described in the introduction that includes a cavity adapted for a chosen gas volume, a light source, and one or more units for receiving light beams and light bundles, wherein said cavity is formed and delimited by a first partially elliptical mirror surface facing towards two partially elliptical mirror surfaces, a second and a third surface, said surfaces being mutually orientated so that a light bundle emitted from the light source will be reflected by said mirror surfaces, preferably a number of times, so as to form an optical measuring path extremity, and terminate in a light bundle receiving unit associated with a chosen optical measuring path extremity.

With the intention of solving one or more of the aforesaid technical problems, it is proposed in accordance with the invention that the light source is disposed within the cavity and then within its one end-region, and that there is disposed in said end-region a reflector which causes the emitted light bundles to converge towards a focusing point.

By way of proposed embodiments that lie within the scope of the inventive concept, it is proposed that the reflector is adapted to allow the light bundles to converge towards a focusing point located within the cavity and within its other, opposite end-region.

It is also proposed that said focusing point shall be located adjacent to but at a given path extremity from a flat cavity-associated mirror part.

In this regard, it is proposed that a virtual focusing point formed by the flat mirror part is located outside said cavity.

According to the invention, the flat mirror part shall be disposed adjacent a first delimiting surface of said first, partially elliptical mirror surface.

The reflector mentioned is comprised of a partially elliptical section adjacent said first, partially elliptical mirror surface.

The reflector is also comprised of a partially elliptical section formed by a wall-part disposed in the cavity.

It is particularly proposed that the cavity is very thin and that it can be formed or produced from at least two mutually co-acting parts.

It is also proposed in accordance with the invention that a first gas connection shall be disposed adjacent said flat mirror part, and that a second gas connection shall be disposed adjacent to the gas source and adjacent the wall-part fastened in the cavity.

It is also proposed in accordance with the present invention that the cavity of the gas cell shall be formed so that the light bundles will be reflected from said virtual, cavity-peripheral focusing point to a border region between the second and the third mirror surface, and that a first part, reflected by the second mirror surface, forms a first optical measuring path extremity, while a second part, reflected by the third mirror surface, forms a second optical measuring path extremity.

According to the invention, a device for deflecting a direct-acting light bundle from the light source is provided adjacent the light source and within the cavity, said device facing towards the flat mirror part, such as to therewith form a further optical measuring path extremity.

It is also proposed in accordance with the invention that cavity-associated active optical surfaces shall be concentrated on their respective sides of the light source and extend towards partially elliptical, reflector-associated sections and, moreover, converge towards the cavity-internal focusing point and a surface region disposed between the three partially elliptical mirror surfaces.

It is also proposed that said device shall be designed and adapted to shadow direct-acting light bundles to cavity-associated light detectors.

According to the invention, the light source may be adapted for infrared radiation and is intended to enable moisture contents to be measured.

The units that receive the light beam or light bundle are adapted to determine the presence of and/or the concentration of other selected gases, such as carbon dioxide, carbon monoxide, nitrous oxide, etc.

Advantages

Those advantages primarily characteristic of an inventive gas cell having characteristic significance of the present invention reside in the provision of conditions capable of providing in a gas cell of small external dimensions at least two long optical measurement path extremities. In addition, measures have been taken for causing a gas volume to pass through the cavity in laminar flow or essentially laminar flow.

The gas cell can also be used to provide a further, albeit short, measurement path extremity.

The primary characteristics of an inventive gas cell are set forth.

BRIEF DESCRIPTION OF THE DRAWINGS

An embodiment at present preferred and having characteristic features significant of the invention will now be described in more detail by way of example and with reference to the accompanying drawings, in which.

DESCRIPTION OF EMBODIMENTS AT PRESENT PREFERRED

Figure 1:
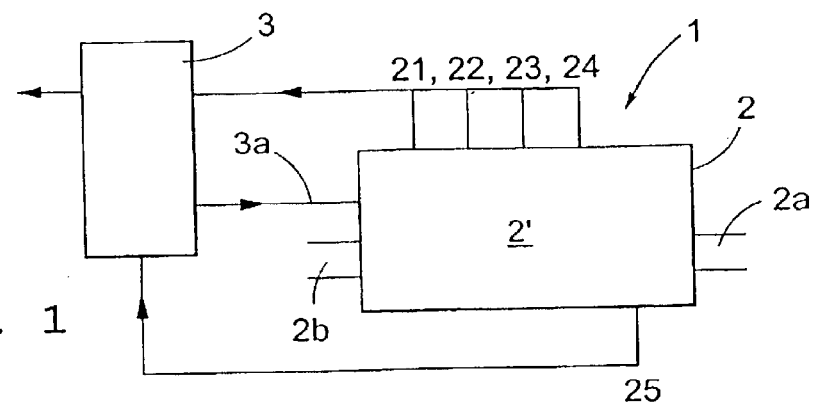
FIG. 1 is a block diagram illustrating a gas detector that uses an inventive gas cell.

Referring to FIG. 1, there is shown schematically a detector arrangement for enabling the presence of a gas and/or a gas concentration in/of a gas mixture to be determined.

The arrangement shown in FIG. 1 is referenced 1 and includes a requisite gas sensor 2 which is connected to a connection 2a and to a connection 2b which enable a volume of gas to be assayed to be delivered to and exited from the gas cell.

By way of an alternative, a wall-part 20' may serve as a diffusion filter or porous medium particle filter, where gas flow is diffused.

It is assumed that the gas is introduced via the connection 2a and allowed to pass through a gas cell 2' in the gas sensor 2 in a more or less laminar flow, and thereafter to exit through the connection 2b.

FIG. 1 also shows the connection of one or more units 21, 22, 23, 24 and 25 to a central processing unit 3, said units being intended to receive light beams or light bundles.

The central unit 3 thus includes necessary signal processing circuits and circuits for emitting and activating a gas sensor associated light source via a line 3a.

The present invention relates primarily to a gas sensor 2' in the gas cell 2, this gas sensor being described in more detail below with reference to FIGS. 2 and 3.

The gas cell 2' includes the cavity 20, which is adapted for a chosen gas volume, a light source 30, and one or more light beam receiving units 21–25.

The cavity 20 is formed and delimited by, inter alia, a first partially elliptical mirror surface 20a and two partially elliptical mirror surfaces, a second 20b and a third 20c, which lie opposite the first mirror surface 20a.

The three mirror surfaces 20a, 20b, 20c are so orientated in relation to each other that the light beam emitted from the light source 30 will be reflected between said mirror surfaces and therewith be able to form an optical measuring path extremity or path extremities, and terminate in a light beam receiving unit or detector to which a chosen measuring path extremity is allocated.

Figure 2:
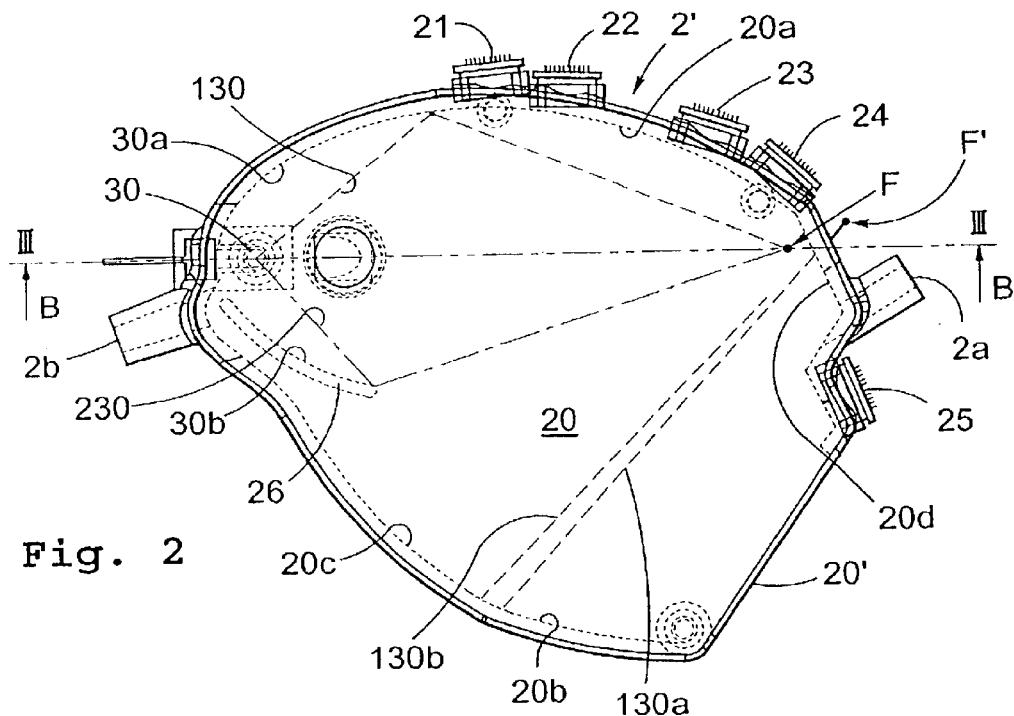
FIG. 2 is a plan view showing the form of an inventive gas cell.

The light source 30 is disposed in one end-region of the cavity, the left region in FIG. 2, and a reflector that causes a chosen light beam to converge is disposed in said one end-region and comprises an upper part 30a, and a lower part 30b, with the light source 30 placed in a focusing point.

The reflector parts 30a, 30b are partially elliptical and adapted to cause the chosen light ray bundles or groups to converge towards a focusing point F in the cavity 20, such as respective light bundles 130 and 230.

The focusing point F is located in the region of the other end of the cavity, to the right in FIG. 2.

The focusing point F is located adjacent a flat cavity-associated mirror part 20d. This flat mirror part 20d is angled somewhat in relation to a straight line between the light source 30 and the focusing point F.

The flat mirror part 20d creates from the focusing point F a virtual focusing point F', which will now be spaced slightly outside the cavity 20, as clearly shown in FIG. 2.

The flat mirror part 20d is disposed adjacent a right-hand delimiting surface of the first mirror surface 20a.

The upper mirror surface 30a of the reflector is comprised of a partially elliptical section and is located adjacent a left-orientated delimiting surface of the first mirror surface 20a.

The reflector-associated part 30b is also comprised of a partially elliptical section formed by a partially elliptical wall-part 26 disposed in the cavity 20.

Figure 3:
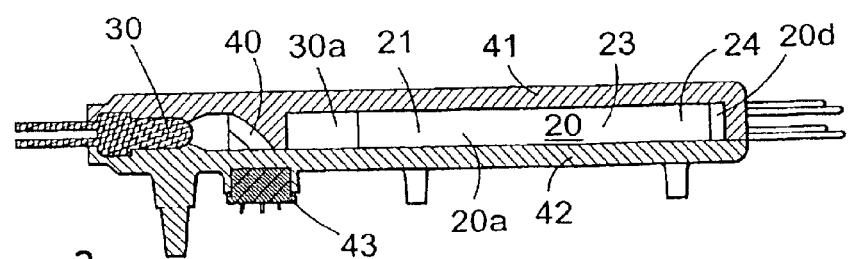
FIG. 3 is a sectioned view taken on the line III—III in FIG. 2.

Referring to FIG. 3, it will be seen that the cavity 20 may be very thin or narrow and that it is defined primarily by two mutually co-acting parts 41, 42. The thickness may conform to the length of an incandescent filament for the light source 30, i.e. a length of 1.5 mm or slightly there above.

A first gas connection 2a is disposed adjacent said flat mirror part 20d.

A second gas connection 2b is disposed adjacent the light source 30 and adjacent the wall-part 26 positioned in the cavity 20.

In addition to forming the mirror part 30b, the wall-part 26 is adapted, as a result of its thickness and shape, to be able to provide a pronounced laminar flow of the gas volume to be assayed, said gas volume being assumed to be introduced through the connection 2a and exited through the connection 2b.

In accordance with the invention, the bundles of light rays, such as the light bundles 130 and 230, are reflected from said virtual focusing part F' to a boundary region located between the second mirror surface 20b and the third mirror surface 20c, and that a first part 130a, reflected by the second mirror surface 20b, forms a first optical measurement path extremity, whereas a second part 130b, reflected by the third mirror surface 20c, forms a second optical measurement path extremity.

As will be understood, each of these optical measurement path extremities may be divided into further measurement path extremities as the light is reflected between the surfaces 20a, 20b and 20c, in a manner known per se. Each optical measurement path extremity terminates in a chosen detector 21, 22, 23, 24 and 25 respectively.

Located adjacent the light source 30 and facing towards the flat mirror part 20d is a device 40 which is angled in respect to direct-acting light bundles so as to be able to form a further (or several) optical measuring path extremity (or path extremities) to a light bundle receiving unit 43.

Figure 4:
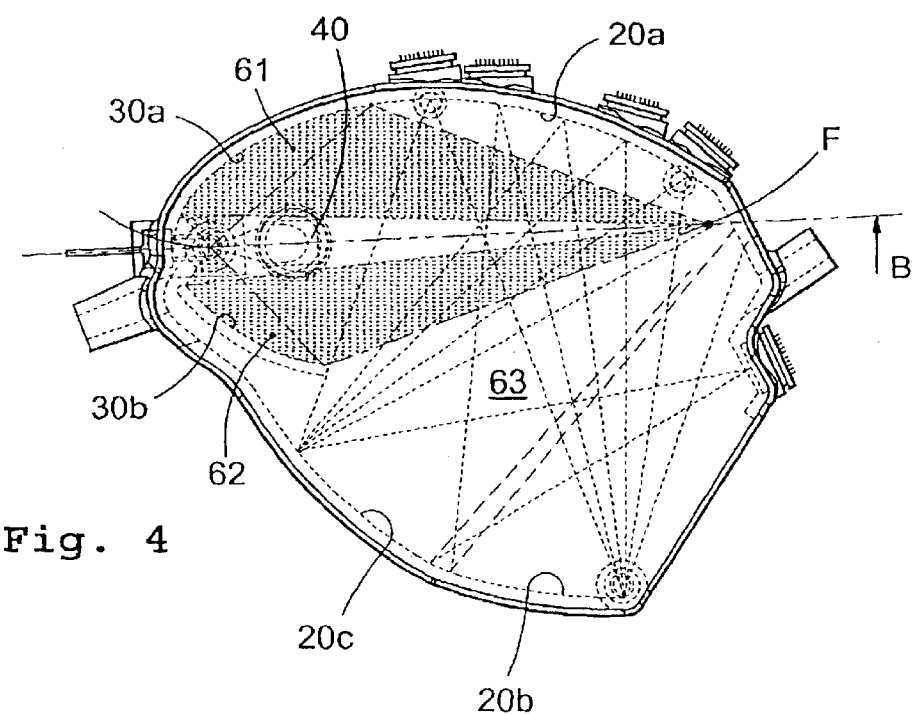
FIG. 4 illustrates a gas cell according to FIG. 1 and shows optically active illuminating surfaces.

Shown in FIG. 4 are cavity-associated active optical surfaces which are each concentrated on a respective side of the light source 30, these surfaces being referenced 61 and 62.

These optical surfaces extend on respective sides of the light source 30 towards the partially elliptical sections 30a, 30b and cover those surfaces that converge towards the focusing point F.

A further optical surface region 63 is defined between the partially elliptical mirror surfaces 20a, 20b and 20c.

Figure 5:
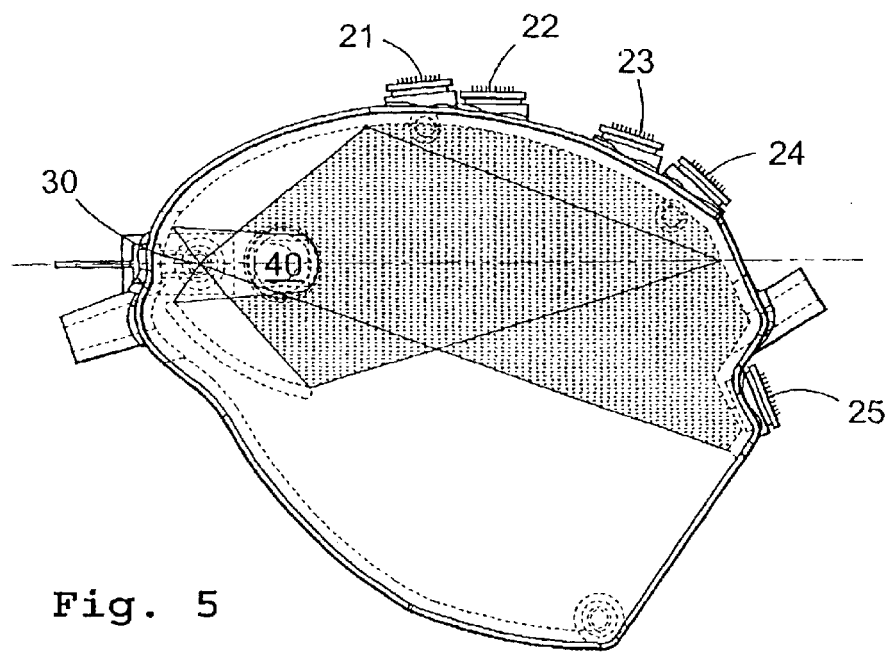
FIG. 5 illustrates the gas cell according to FIG. 2 showing active illumination surfaces and a periscope shadow formed by a device, and the surface area within which direct radiation from the light source onto light detectors or units shall be prevented.

It will be seen particularly from FIG. 5 that said device 40 is adapted to enable shadowing of the direct-acting light bundles to the cavity-associated light detectors 21–25.

The light source 30 may be adapted for infrared radiation and intended, in this regard, for measuring the moisture content of the cavity-enclosed gas volume, i.e. measurement of the water vapour concentration.

The selected bundles of light rays may also be adapted to enable the presence of and/or the concentrations of another chosen gas to be determined, such as carbon dioxide, carbon monoxide, nitrous oxide, through the medium of said light-receiving circuits or units.

Referring back to FIGS. 2 and 3, it will be noted that the additional optical measurement path extremity, between the light source 30 and the unit 43 can be given a short length, such as a length of 4–20 mm or about 8 mm.

The optical measurement path extremity to the unit 21 or 23 may be given a length of 13 or 21 cm respectively, and the optical measurement path extremity between the light source 30 and respective units 23, 24, 25 may be given a length of 21, 29 or 37 cm respectively.

It will also be noted that in the case of a gas cell 2' having external measurements of about 45×45 mm, it is therewith possible to provide at least two mutually independent optical measurement path extremities that have a length of 36 cm, so as to be able to determine the concentration of nitrous gas/carbon dioxide and the water content of the gas and its carbon dioxide concentration.

It will be understood that the invention is not restricted to the aforedescribed exemplifying embodiment thereof and that modifications can be made within the scope of the inventive concept as illustrated in the accompanying claims.

What is claimed is:

1. A gas cell that includes a cavity adapted for a chosen gas volume, a light source, and units for receiving one or more bundles of light rays, wherein the cavity is formed and delimited by, inter alia, a first partially elliptical mirror surface, two partially elliptical mirror surfaces, a second surface and the third surface, disposed opposite to said first surface and oriented in relation to each other so that light bundles emitted from the light source will be reflected by said mirror surfaces to form an optical measurement path extremity and terminate in a unit (21–25) that receives an allocated light bundle in a chosen measurement path extremity, wherein said light source is disposed in one end-region of said cavity; and a reflector disposed in said one end-region that causes the emitted light bundles to converge towards a focusing point.

2. A gas cell according to claim 1, wherein said reflector is adapted to cause said light bundles to converge towards a focusing point located within the cavity.

3. A gas cell according to claim 2, wherein said focusing point is located adjacent a flat cavity-associated mirror part.

4. A gas cell according to claim 1, wherein a virtual focusing point formed by a mirror section is located outside said cavity.

5. A gas cell according to claim 1, wherein said mirror surfaces include a flat mirror section disposed adjacent a delimiting surface of said first mirror surface.

6. A gas cell according to claim 1, wherein said reflector is comprised of a partially elliptical section oriented adjacent said first mirror surface.

7. A gas cell according to claim 1, wherein said reflector is comprised of a partially elliptical section formed by a wall-part disposed within said cavity.

8. A gas cell according to claim 1, wherein said cavity is thin and formed by at least two parts that can co-act with one another.

9. A gas cell according to claim 1, wherein said mirror surface include a flat mirror section, further comprising a gas connection disposed adjacent said flat mirror section.

10. A gas cell according to claim 1, wherein a gas connection is disposed adjacent said light source and adjacent a wall section disposed within the cavity.

11. A gas cell according to claim 1, wherein said light bundles are reflected from said virtual focusing point to a border region oriented between said second and said third mirror surfaces; and a first part, reflected by said second mirror surface, forms a first optical measurement path extremity, while a second part, reflected by the third mirror surface, forms a second optical measurement path extremity.

12. A gas cell according to claim 1, wherein said mirror surfaces include a flat mirror section, further comprising a device located adjacent said light source and functioning to deflect a light bundle emitted from said light source in a direction towards said flat mirror section, therewith to form a further optical measurement path extremity.

13. A gas cell according to claim 12, further comprising cavity-associated light detectors and said device is adapted to allow shadowing of direct-acting light bundles to said cavity-associated light detectors.

14. A gas cell according to claim 1, further comprising cavity-associated active optical surfaces that are concentrated on respective sides of said light source and towards partially elliptical reflector-adapted sections and that converge towards a focusing point, said optical surfaces being comprised of a surface region located between said elliptical mirror surfaces.

15. A gas cell according to claim 1, wherein said light source is adapted for infrared radiation and intended for determining moisture content or steam via a selected detector.

16. A gas cell according to claim 1, further comprising selected units or detectors for receiving said light bundles and being adapted to determine the concentration of a chosen gas selected from the group consisting of carbon dioxide, carbon monoxide and nitrous oxide.

17. A gas cell according to claim 1, wherein a cavity-associated wall section is comprised of a diffusion filter.

18. A gas cell according to claim 1, wherein the thickness of said cavity is adapted to the length of an incandescent filament for the light source.

* * * * *